United States Patent
Ahmed et al.

(10) Patent No.: US 9,370,492 B2
(45) Date of Patent: Jun. 21, 2016

(54) SOLID PHARMACEUTICAL DOSAGE FORMS COMPRISING BISPHOSPHONATES AND MODIFIED AMINO ACID CARRIERS

(75) Inventors: Hashim Ahmed, Princeton, NJ (US); Lewis Bender, Redding, CT (US); Martin Howard Infeld, Upper Montclair, NJ (US); Shingai Majuru, Brewster, NY (US); Wantanee Phuapradit, Montville, NJ (US); Navnit Hargovindas Shah, Clifton, NJ (US); Zhongshui Yu, Williston Park, NY (US)

(73) Assignee: EMISPHERE TECHNOLOGIES, INC., Roseland, NJ (US)

( * ) Notice: Subject to any disclaimer, the term of this patent is extended or adjusted under 35 U.S.C. 154(b) by 758 days.

(21) Appl. No.: 12/504,484

(22) Filed: Jul. 16, 2009

(65) Prior Publication Data

US 2009/0281064 A1  Nov. 12, 2009

Related U.S. Application Data

(63) Continuation of application No. 11/498,445, filed on Aug. 3, 2006, now abandoned.

(60) Provisional application No. 60/710,899, filed on Aug. 24, 2005, provisional application No. 60/763,982, filed on Feb. 1, 2006.

(51) Int. Cl.
| | |
|---|---|
| *A01N 57/00* | (2006.01) |
| *A61K 31/66* | (2006.01) |
| *A61K 9/20* | (2006.01) |
| *A61K 9/16* | (2006.01) |
| *A61K 9/48* | (2006.01) |
| *A61K 9/50* | (2006.01) |
| *A61K 31/663* | (2006.01) |
| *A61K 31/675* | (2006.01) |
| *A61K 47/32* | (2006.01) |
| *A61K 9/28* | (2006.01) |
| *A61K 47/18* | (2006.01) |

(52) U.S. Cl.
CPC ............ *A61K 9/2013* (2013.01); *A61K 9/1617* (2013.01); *A61K 9/48* (2013.01); *A61K 9/501* (2013.01); *A61K 31/663* (2013.01); *A61K 31/675* (2013.01); *A61K 47/32* (2013.01); *A61K 9/2866* (2013.01); *A61K 47/183* (2013.01)

(58) Field of Classification Search
USPC ........................................................ 514/108
See application file for complete search history.

(56) References Cited

U.S. PATENT DOCUMENTS

| | | |
|---|---|---|
| 4,927,814 A | 5/1990 | Gall et al. |
| 5,451,410 A | 9/1995 | Milstein et al. |
| 5,650,386 A | 7/1997 | Leone-Bay et al. |
| 5,766,633 A | 6/1998 | Milstein et al. |
| 5,792,451 A | 8/1998 | Sarubbi et al. |
| 5,866,536 A | 2/1999 | Leone-Bay et al. |
| 5,965,121 A | 10/1999 | Leone-Bay et al. |
| 5,989,539 A | 11/1999 | Leone-Bay et al. |
| 6,001,347 A | 12/1999 | Leone-Bay et al. |
| 6,099,856 A | 8/2000 | Milstein et al. |
| 6,344,213 B1 | 2/2002 | Leone-Bay et al. |
| 6,346,242 B1 | 2/2002 | Leone-Bay et al. |
| 6,623,731 B2 | 9/2003 | Leone-Bay et al. |
| 6,699,467 B2 | 3/2004 | Leone-Bay et al. |
| 2004/0097468 A1 | 5/2004 | Wimalawansa |
| 2004/0147484 A1* | 7/2004 | Boyd et al. ................ 514/75 |
| 2006/0166938 A1* | 7/2006 | Bauss et al. ................ 514/89 |

FOREIGN PATENT DOCUMENTS

| | | | |
|---|---|---|---|
| WO | 00/46182 A1 | 8/2000 | |
| WO | 00/59863 A1 | 10/2000 | |

OTHER PUBLICATIONS

Body (Expert Opinion on Pharmacotherapy (2003) 4:567-580).*
Nussbaum et. al. (Journal of Clinical Oncology (1993) 11:1618-1623).*
U.S. Appl. No. 60/569,476, filed May 6, 2004.
U.S. Appl. No. 60/619,418, filed Oct. 15, 2004.
Ansel, H., et al., Pharmaceutical Dosage Forms and Drug Delivery Systems, 6th Ed., 1995, pp. 66, 105-110, 196, and 456-457.

* cited by examiner

*Primary Examiner* — Marcos Sznaidman
(74) *Attorney, Agent, or Firm* — Blank Rome LLP

(57) ABSTRACT

The present invention provides novel solid pharmaceutical dosage forms for oral administration comprising a bisphosphonate, or a pharmaceutically acceptable salt thereof, which bisphosphonate is present in an amount not therapeutically effective when the bisphosphonate is orally administered alone, and a modified amino acid carrier, or a pharmaceutically acceptable salt thereof, which modified amino acid carrier is present in an amount effective to facilitate absorption of the bisphosphonate in the gastrointestinal tract such that the bisphosphonate is therapeutically effective. The ratio of bisphosphonate to modified amino acid carrier is from about 1:30 to about 1:1, respectively. These novel solid pharmaceutical dosage forms are useful in the treatment or control of bone diseases and particular disorders in calcium metabolism, including, for example, osteoporosis, hypercalcaemia of cancer, and the treatment of metastatic bone pain. The present invention also provides a method for treating these diseases employing the solid pharmaceutical dosage forms and a method for preparing the pharmaceutical dosage forms.

3 Claims, No Drawings

SOLID PHARMACEUTICAL DOSAGE FORMS COMPRISING BISPHOSPHONATES AND MODIFIED AMINO ACID CARRIERS

PRIORITY TO RELATED APPLICATIONS

This application is a continuation of U.S. patent application Ser. No. 11/498,445, filed Aug. 3, 2006, which claims the benefit of U.S. Provisional Application No. 60/710,899, filed Aug. 24, 2005 and U.S. Provisional Application No. 60/763,982, filed Feb. 1, 2006. The entire contents of the above-identified applications are hereby incorporated by reference.

FIELD OF THE INVENTION

The present invention relates to pharmaceutical compositions and methods for making same.

BACKGROUND OF THE INVENTION

Bisphosphonates

Bisphosphonates (diphosphonates) are synthetic compounds characterized by two carbon to phosphorus bonds:

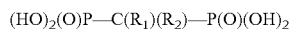

$(HO)_2(O)P—C(R_1)(R_2)—P(O)(OH)_2$

Bisphosphonates are analogs of inorganic pyrophosphate.

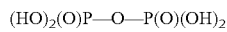

$(HO)_2(O)P—O—P(O)(OH)_2$

Inorganic pyrophosphate is a normal by-product of human metabolism and is produced by anabolic processes. Inorganic pyrophosphate is readily hydrolyzed to its constituent phosphate groups. When the linking oxygen atom in the pyrophosphate molecule is replaced by a carbon atom, the bisphosphonate formed is resistant to hydrolysis and is chemically stable. Like pyrophosphate, bisphosphonates bind to the hydroxyapatite crystals of bone and prevent their growth and their dissolution.

Bisphosphonates are highly effective in enhancing bone mineral density (BMD) and decreasing bone fracture rates. Bisphosphonates are effective drugs for bone disorders characterized by increased bone resorption, such as Paget's disease, osteoporosis, hypercalcaemia of cancer, metastatic bone disease, multiple myeloma, and bony metastases. Bisphosphonates are also effective in the treatment of bone pain accompanying these disorders.

Due to their stability, the bisphosphonates are absorbed, stored and excreted unchanged. Bisphosphonates are characterized by poor intestinal absorption but highly selective localization and prolonged storage in bone. Absorption is believed to take place in the stomach and upper small intestine, and is reduced if the drug is given with antacids, calcium, magnesium, iron supplements, or vitamins with minerals. A period of about 2 hours of fasting is generally recommended before taking the bisphosphonate and a period of about 30-60 minutes of sitting or standing upright is generally recommended after taking the bisphosphonate to avoid irritation of the throat and esophagus. Bisphosphonates are therefore not administered at meal times or with dairy products.

United States patent publication number 20040097468, paragraph 10, discloses that the absorption of bisphosphonates is usually less than 1% of that of the orally or intravenously administered dose and therefore it may take several months or up to a year or more to get an adequate amount of a bisphosphonate into bone to be therapeutically effective.

Modified Amino Acid Carriers

Delivery of an active agent is often limited by biological, chemical, and/or physical barriers. The barrier may be imposed by the nature of the active agent, by the nature of the target, by the environment of the target, or by the environment through which delivery of the active agent occurs. Biological barriers include the properties of the active agent; chemical barriers include pH variations, lipid bilayers, and degrading enzymes; and physical barriers include organ membranes that must be traversed before the active agent can reach the target. These barriers are of particular significance when the active agent is delivered orally because of varying pH in the gastrointestinal tract, digestive enzymes, and impermeable gastrointestinal membranes.

Many methods for orally administering a pharmacological agent rely upon the co-administration of an adjuvant to artificially increase the permeability of the intestinal wall or the co-administration of an enzymatic inhibitor. The use of liposomes and microspheres of artificial polymers of mixed amino acids (proteinoids) has been disclosed to protect active agents in drug delivery systems. Modified amino acid carriers have also been disclosed to deliver active agents and are disclosed in U.S. Pat. Nos. 5,650,386, 5,866,536, 5,965,121, 5,989,539, 6,001,347, 6,344,213, 6,346,242, 6,623,731, and 6,699,467. Other delivery agents have been disclosed in U.S. Pat. Nos. 5,451,410, 5,766,633, 5,792,451, and 6,099,856. Compositions for delivering bisphosphonates are disclosed in United States patent publication number 2004/0147484.

SUMMARY OF THE INVENTION

The present invention provides a solid pharmaceutical dosage form for oral administration comprising:

(a) a bisphosphonate, or a pharmaceutically acceptable salt thereof, which bisphosphonate is present in an amount not therapeutically effective when the bisphosphonate is orally administered alone; and (b) a modified amino acid carrier, or a pharmaceutically acceptable salt thereof, which modified amino acid carrier is present in an amount effective to facilitate absorption of the bisphosphonate in the gastrointestinal tract such that the bisphosphonate is therapeutically effective;

wherein the ratio of bisphosphonate to modified amino acid carrier is from about 1:30 to about 1:1, respectively.

The present invention also provides a method for treating osteoporosis comprising administering to a subject, in need thereof, a solid pharmaceutical dosage form for oral administration comprising:

(a) a bisphosphonate, or a pharmaceutically acceptable salt thereof, which bisphosphonate is present in an amount not therapeutically effective when the bisphosphonate is orally administered alone; and (b) a modified amino acid carrier, or a pharmaceutically acceptable salt thereof, which modified amino acid carrier is present in an amount effective to facilitate absorption of the bisphosphonate in the gastrointestinal tract such that the bisphosphonate is therapeutically effective;

wherein the ratio of bisphosphonate to modified amino acid carrier is from about 1:30 to about 1:1, respectively.

The present invention further provides a method for treating hypercalcemia of cancer comprising administering to a subject, in need thereof, a solid pharmaceutical dosage form for oral administration comprising:

(a) a bisphosphonate, or a pharmaceutically acceptable salt thereof, which bisphosphonate is present in an amount not therapeutically effective when the bisphosphonate is orally administered alone; and (b) a modified amino acid carrier, or a pharmaceutically acceptable salt thereof, which modified amino acid carrier is present in an amount effective to facilitate absorption of the bisphosphonate in the gastrointestinal tract such that the bisphosphonate is therapeutically effective;
wherein the ratio of bisphosphonate to modified amino acid carrier is from about 1:30 to about 1:1, respectively.

The present invention still further provides a method for treating metastatic bone pain comprising administering to a subject, in need thereof, a solid pharmaceutical dosage form for oral administration comprising:

(a) a bisphosphonate, or a pharmaceutically acceptable salt thereof, which bisphosphonate is present in an amount not therapeutically effective when the bisphosphonate is orally administered alone; and (b) a modified amino acid carrier, or a pharmaceutically acceptable salt thereof, which modified amino acid carrier is present in an amount effective to facilitate absorption of the bisphosphonate in the gastrointestinal tract such that the bisphosphonate is therapeutically effective;
wherein the ratio of bisphosphonate to modified amino acid carrier is from about 1:30 to about 1:1, respectively.

The present invention still further provides a method for preparing a solid pharmaceutical dosage form for oral administration comprising admixing:

(a) a bisphosphonate, or a pharmaceutically acceptable salt thereof, which bisphosphonate is present in an amount not therapeutically effective when the bisphosphonate is orally administered alone; and (b) a modified amino acid carrier, or a pharmaceutically acceptable salt thereof, which modified amino acid carrier is present in an amount effective to facilitate absorption of the bisphosphonate in the gastrointestinal tract such that the bisphosphonate is therapeutically effective;
wherein the ratio of bisphosphonate to modified amino acid carrier is from about 1:30 to about 1:1, respectively.

DETAILED DESCRIPTION OF THE INVENTION

The present invention provides a solid pharmaceutical dosage form for oral administration comprising a bisphosphonate, or a pharmaceutically acceptable salt thereof, which bisphosphonate is present in an amount not therapeutically effective when the bisphosphonate is orally administered alone; and a modified amino acid carrier, or a pharmaceutically acceptable salt thereof, which modified amino acid carrier is present in an amount effective to facilitate absorption of the bisphosphonate in the gastrointestinal tract such that the bisphosphonate is therapeutically effective. The ratio of bisphosphonate to modified amino acid carrier is from about 1:30 to about 1:1, respectively. These novel solid pharmaceutical dosage forms are useful in the treatment or control of bone diseases characterized by increased bone resorption, such as osteoporosis and hypercalcaemia of cancer, as well as the treatment or control of pain that accompanies such disorders. The present invention also provides a method for treating such disorders employing the solid pharmaceutical dosage forms and a method for preparing the pharmaceutical dosage forms.

Oral administration of the bisphosphonate with the modified amino acid carrier results in an increased bioavailability of the bisphosphonate compared to oral administration of the bisphosphonate alone, thereby enabling a lowering of the dose of the bisphosphonate while still achieving equivalent efficacy of the bisphosphonate. Oral administration of the bisphosphonate with the modified amino acid carrier may result in a reduction of the approximately 2 hour period of fasting before taking the bisphosphonate and is expected to reduce the approximately 30-60 minute period of sitting or standing upright after taking the bisphosphonate.

As used herein, the following terms have the given meanings:

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per practice in the art. Alternatively, "about" with respect to the formulations can mean a range of up to 10%, preferably up to 5%.

The term "an amount effective to facilitate absorption of the bisphosphonate in the gastrointestinal tract such that the bisphosphonate is therapeutically effective" as applied to a modified amino acid carrier means an amount of the carrier that increases absorption of the bisphosphonate in the gastrointestinal tract such as to reduce the amount of bisphosphonate as compared to the amount of bisphosphonate required if administered alone to achieve a therapeutic effect.

The term "bisphosphonate" (diphosphonate) refers to compounds characterized by the formula: $(HO)_2(O)P—C(R_1)(R_2)—P(O)(OH)_2$, including pharmaceutically acceptable salts, racemic mixtures, and pure enantiomers thereof, wherein $R_1$ and $R_2$ are defined below.

The term "bisphosphonate is present in an amount not therapeutically effective when the bisphosphonate is orally administered alone" means an amount of a bisphosphonate, or a pharmaceutically acceptable salt thereof, which is not effective to treat, prevent, alleviate or ameliorate symptoms of disease. For example, the therapeutically effective amount of ibandronate for the treatment of osteoporosis is 2.5 mg daily or 150 mg monthly, as measured by the weight of the free acid. Amounts of ibandronate less than the above, for their respective dosage periods, would not be considered therapeutically effective. "[W]hen the bisphosphonate is orally administered alone" means when the bisphosphonate is not orally administered with an agent that facilitates absorption of the bisphosphonate in the gastrointestinal tract. This term does not exclude conventional additives normally included in such formulations including, but not limited to, lactose monohydrate, croscarmellose sodium, povidone, water, sodium stearyl fumarate, and the like. Preferred oral dosage forms are tablets, most preferably tablets containing povidone.

The term "intimate contact" means a close physical association between the bisphosphonate and the modified amino acid carrier. Such intimate contact may be achieved by granulation, spray drying, fluid bed coating, fluid bed layering, and the like, of the bisphosphonate with the modified amino acid carrier.

The term "modified amino acid carriers" refers to modified amino acids, preferably co-amino acids, modified by acylation or sulfonation of the amino group, particularly with phenyl or cyclohexyl groups, wherein the phenyl or cyclohexyl groups may contain a variety of substituents such as hydroxyl, methyl, fluoro, and/or chloro.

The term "pharmaceutically acceptable," such as pharmaceutically acceptable carrier, excipient, etc., means pharmacologically acceptable and substantially non-toxic to the subject to which the particular compound is administered.

The term "pharmaceutically acceptable salt" refers to conventional acid-addition salts of base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium, and quaternary ammonium hydroxides, such as for example, tetramethylammonium hydroxide. Chemical modification of a pharmaceutical compound (i.e., drug) into a salt is a technique well known to pharmaceutical chemists to obtain improved physical and chemical stability, hygroscopicity, and solubility of compounds. See, e.g., H. Ansel et. al., Pharmaceutical Dosage Forms and Drug Delivery Systems (6$^{th}$ Ed. 1995) at pp. 66, 105-110, 196 and 456-457.

The term "prodrug" refers to compounds that undergo biotransformation prior to exhibiting their pharmacological effects. The chemical modification of drugs to overcome pharmaceutical problems has also been termed "drug latentiation." Drug latentiation is the chemical modification of a biologically active compound to form a new compound, which upon in vivo enzymatic attack will liberate the parent compound. The chemical alterations of the parent compound are such that the change in physicochemical properties will affect the absorption, distribution and enzymatic metabolism. The definition of drug latentiation has also been extended to include nonenzymatic regeneration of the parent compound. Regeneration takes place as a consequence of hydrolytic, dissociative, and other reactions not necessarily enzyme mediated. The terms prodrugs, latentiated drugs, and bioreversible derivatives are used interchangeably. By inference, latentiation implies a time lag element or time component involved in regenerating the bioactive parent molecule in vivo. The term prodrug is general in that it includes latentiated drug derivatives as well as those substances that are converted after administration to the actual substance which combines with receptors. The term prodrug is a generic term for agents, which undergo biotransformation prior to exhibiting their pharmacological actions.

The term "SNAC" as used herein refers to N-(8-[2-hydroxybenzoyl]-amino) caprylic acid and pharmaceutically acceptable salts thereof, including its monosodium and disodium salt. The term "SNAC free acid" refers to N-(8-[2-hydroxybenzoyl]-amino) caprylic acid. Unless otherwise noted, the term "SNAC" refers to all forms of SNAC, including all amorphous and polymorphic forms of SNAC, such as SNAC trihydrate and those described in U.S. Ser. Nos. 60/619,418 and 60/569,476, both of which, to the extent necessary, are hereby incorporated by reference.

The term "SNAC trihydrate" as used herein refers to a crystalline form of SNAC in which three molecules of water are associated with each molecule of SNAC. SNAC can be prepared by the procedures described in U.S. Pat. No. 5,650,386 and International Publication Nos. WO00/46182 and WO00/59863).

The term "therapeutically effective amount" with respect to a bisphosphonate means an amount of the compound, or a pharmaceutically acceptable salt thereof, which is effective to treat, prevent, alleviate or ameliorate symptoms of disease, either alone or in combination with a carrier, such as a modified amino acid carrier.

As set out above, the present invention provides a novel solid pharmaceutical dosage form for oral administration comprising a bisphosphonate, or a pharmaceutically acceptable salt thereof, which bisphosphonate is present in an amount not therapeutically effective when the bisphosphonate is orally administered alone; and a modified amino acid carrier, or a pharmaceutically acceptable salt thereof, which modified amino acid carrier is present in an amount effective to facilitate absorption of the bisphosphonate in the gastrointestinal tract such that the bisphosphonate is therapeutically effective. The ratio of bisphosphonate to modified amino acid carrier is from about 1:30 to about 1:1, respectively. Preferably, the pharmaceutical dosage form is administered to a mammal, more preferably, the pharmaceutical dosage form is administered to a human.

The bisphosphonates in the present invention may be selected from a wide variety of bisphosphonates and pharmaceutically acceptable salts thereof. Bisphosphonates may be represented by the formula: $(HO)_2(O)P-C(R_1)(R_2)-P(O)(OH)_2$. In the above formula, $R_1$ may be selected from the group consisting of OH, Cl, and H; and $R_2$ may be selected from the group consisting of $(CH_2)_3NH_2$, Cl, $CH_2$-1-pyrrolidinyl, $CH_3$, $CH_2CH_2N(CH_3)(CH_2CH_2CH_2CH_2CH_3)$, N-cycloheptyl, H, $(CH_2)_5NH_2$, $(CH_2)_2N(CH_3)_2$, $(CH_2)_2NH_2$, $CH_2$-3-pyridinyl, S4-chlorophenyl, $CH_2$-2-imidazo-pyridinyl, and $CH_2$-2-imidazolyl. Illustrative nonlimiting examples of bisphosphonates include alendronate [Fosamax®, $R_1$=OH, $R_2$=$(CH_2)_3NH_2$], clodronate [$R_1$=$C_1$, $R_2$=Cl], EB-1053 [$R_1$=OH, $R_2$=$CH_2$-1-pyrrolidinyl], etidronate [Didrocal®, $R_1$=OH, $R_2$=$CH_3$], ibandronate [Boniva®, $R_1$=OH, $R_2$=$CH_2CH_2N(CH_3)(CH_2CH_2CH_2CH_2CH_3)$], incadronate [$R_1$=H, $R_2$=N-cycloheptyl], medronate [$R_1$=H, $R_2$=H], neridronate [$R_1$=OH, $R_2$=$(CH_2)_5NH_2$], olpadronate [$R_1$=OH, $R_2$=$(CH_2)_2N(CH_3)_2$], pamidronate [Aredia®, $R_1$=OH, $R_2$=$(CH_2)_2NH_2$], risedronate [Actonel®, $R_1$=OH, $R_2$=$CH_2$-3-pyridinyl], tiludronate [Skelid®, $R_1$=H, $R_2$=S4-chlorophenyl], YH529 [$R_1$=OH, $R_2$=$CH_2$-2-imidazo-pyridinyl], and zoledronate [Zometa®, $R_1$=OH, $R_2$=$CH_2$-2-imidazolyl]. Preferably, the bisphosphonate is alendronate or ibandronate, or a pharmaceutically acceptable salt thereof. More preferably, the bisphosphonate is ibandronate, or a pharmaceutically acceptable salt thereof.

Bisphosphonates inhibit osteoclast-mediated bone resorption. In osteoporosis, where osteoclasts break down bone quickly, inhibition of this pathway has been shown to slow bone turnover leading not only to an attenuation of turnover but also to a mean increase in bone mass. Bisphosphonates have a high binding affinity for hydroxyapatite, a calcium compound, which is part of the mineral matrix of bone. Binding to the site allows the drug to be taken up by mature osteoclasts during the resorption process, and to act intracellularly as an isoprenoid diphosphate lipid analogue, disrupting the farnesylation and geranylgeranylation of small GTPase signaling proteins and potentiating selective osteoclast apoptosis. Clinical studies indicate that bisphosphonates increase bone mineral density (BMD) of the existing skeleton and reduce the risk of spine fractures for postmenopausal women with osteoporosis. In postmenopausal women with very severe osteoporosis, bisphosphonates reduce the risk of fractures throughout the skeleton.

Ibandronate is disclosed in U.S. Pat. No. 4,927,814, which disclosure is incorporated herein by reference. Ibandronate may be represented by the following formula:

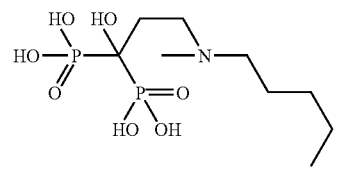

Ibandronate is commercialized as the sodium salt, 3-(N-methyl-N-pentyl)amino-1-hydroxypropane-1,1-diphosphonic acid, monosodium salt, monohydrate (Boniva®). Ibandronate has the molecular formula $C_9H_{22}NO_7P_2Na \cdot H_2O$ and a molecular weight of 359.24. Ibandronate sodium is a white- to off-white powder, which is freely soluble in water and practically insoluble in organic solvents.

The modified amino acid carriers in the present invention may be selected from a wide variety of modified amino acids, and pharmaceutically acceptable salts thereof. The modified amino acids are preferably ω-amino acids modified by acylation or sulfonation of the amino group, particularly with phenyl or cyclohexyl groups. The phenyl or cyclohexyl groups may contain a variety of substituents such as hydroxy, methyl, fluoro, and chloro. Modified amino acid carriers useful in the present invention are disclosed in U.S. Pat. Nos. 5,650,386, 5,866,536, 5,965,121, 5,989,539, 6,001,347, 6,344,213, 6,346,242, 6,623,731, and 6,699,467, which disclosures are incorporated herein by reference.

The modified amino acids of the present invention are preferably represented by formula (I):

$$HOOC—R_1—N(R_2)—X—R_3 \quad (1)$$

In formula (1):

X is CO or $SO_2$; preferably X is CO.

$R_1$ is selected from the group consisting of $C_3$-$C_{24}$ alkyl, $C_2$-$C_{20}$ alkenyl, $C_2$-$C_{20}$ alkyne, $C_5$-$C_6$ cycloalkyl, phenyl, and naphthyl; preferably $R_1$ is $C_3$-$C_{11}$ alkyl; more preferably $R_1$ is $C_3$-$C_8$ alkyl; and most preferably $R_1$ is $C_7$-$C_8$ alkyl.

$R_2$ is selected from the group consisting of hydrogen, $C_1$-$C_4$ alkyl, and $C_2$-$C_4$ alkenyl; preferably $R_2$ is hydrogen or $C_1$-$C_4$ alkyl; more preferably $R_2$ is hydrogen or $C_1$-$C_2$ alkyl; and most preferably $R_2$ is hydrogen.

$R_3$ is selected from the group consisting of $C_1$-$C_7$ alkyl, $C_3$-$C_{10}$ cycloalkyl, phenyl, thienyl, pyrrolyl, and pyridinyl; wherein $R_3$ may be substituted by substituents selected from the group consisting of $C_1$-$C_5$ alkyls, $C_2$-$C_4$ alkenyls, F, Cl, OH, $SO_2$, COOH, and $SO_3H$. Preferably, $R_3$ is 2-hydroxyphenyl.

A preferred modified amino acid carrier in the present invention is sodium N-(8-(2-hydroxybenzoyl)amino)caprylate (SNAC), which is disclosed in U.S. Pat. No. 5,650,386, which disclosure is incorporated herein by reference. N-(8-(2-hydroxybenzoyl)amino)caprylate has the structure set out below.

Another preferred modified amino acid carrier is N-(10-(2-hydroxybenzoyl)amino)capricate, which is disclosed in U.S. Pat. Nos. 5,866,536 and 6,344,213, which disclosures are incorporated herein by reference. N-(10-(2-hydroxybenzoyl)amino)capricate has the structure set out below.

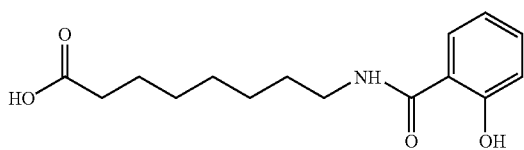 [SMILES: O=C(O)CCCCCCCNC(=O)c1ccccc1O]

Another preferred modified amino acid carrier is N-(2-methoxybenzoyl)-3-(4-aminophenyl)proprionate, which is disclosed in U.S. Pat. No. 5,965,121, which disclosure is incorporated herein by reference. N-(2-methoxybenzoyl)-3-(4-aminophenyl)proprionate has the structure set out below.

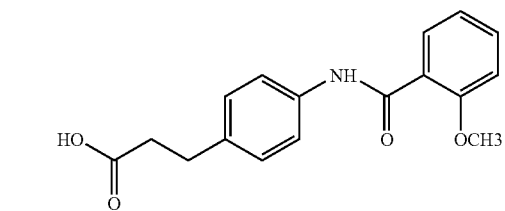 [SMILES: COc1ccccc1C(=O)Nc1ccc(CCC(=O)O)cc1]

Another preferred modified amino acid carrier is N-(3-dimethylaminobenzoyl)-3-(4-aminophenyl)butyrate, which is disclosed in U.S. Pat. No. 5,989,539, which disclosure is incorporated herein by reference. N-(3-dimethylaminobenzoyl)-3-(4-aminophenyl)butyrate has the structure set out below.

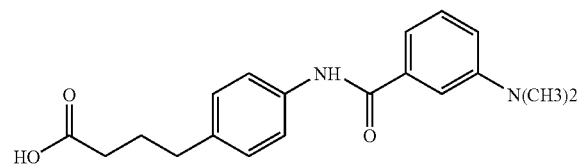 [SMILES: CN(C)c1cccc(C(=O)Nc2ccc(CCCC(=O)O)cc2)c1]

Another preferred modified amino acid carrier is N-(2-methoxybenzoyl)-3-(4-aminophenyl)butyrate, which is disclosed in U.S. Pat. No. 6,001,347, which disclosure is incorporated herein by reference. N-(2-methoxybenzoyl)-3-(4-aminophenyl)butyrate has the structure set out below.

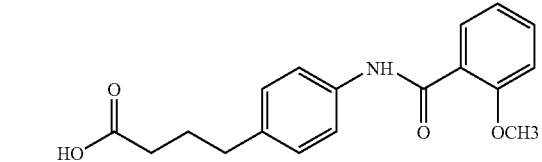 [SMILES: COc1ccccc1C(=O)Nc1ccc(CCCC(=O)O)cc1]

Another preferred modified amino acid carrier is N-(2-aminobenzoyl)-3-(4-aminophenyl)butyrate, which is disclosed in U.S. Pat. No. 6,346,242, which disclosure is incorporated herein by reference. N-(2-aminobenzoyl)-3-(4-aminophenyl)butyrate has the structure set out below.

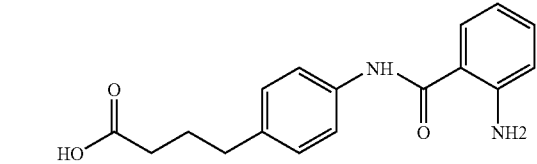 [SMILES: Nc1ccccc1C(=O)Nc1ccc(CCCC(=O)O)cc1]

Another preferred modified amino acid carrier is N-(4-(3-cyclohexyl-propionyl)amino)butyrate, which is disclosed in U.S. Pat. No. 6,623,731, which disclosure is incorporated herein by reference. N-(4-(3-cyclohexyl-propionyl)amino)butyrate has the structure set out below.

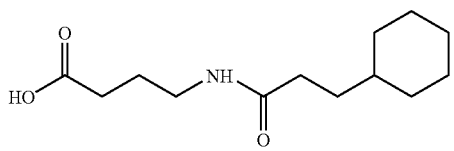 [SMILES: O=C(O)CCCNC(=O)CCC1CCCCC1]

Another preferred modified amino acid carrier is N-(6-(4-methylcyclohexyl-carbonyl)amino)caproate, which is disclosed in U.S. Pat. No. 6,699,467, which disclosure is incorporated herein by reference. N-(6-(4-methylcyclohexyl-carbonyl)amino)caproate has the structure set out below.

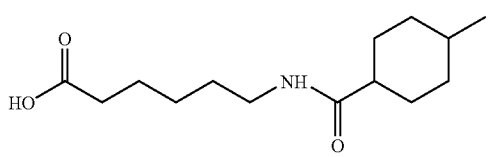 [SMILES: CC1CCC(C(=O)NCCCCCC(=O)O)CC1]

The most preferred modified amino acid carrier is sodium N-(8-(2-hydroxybenzoyl)amino)caprylate (SNAC).

The ratio of bisphosphonate to modified amino acid carrier is such that absorption of the orally administered bisphosphonate in the gastrointestinal tract is facilitated over that of absorption of the bisphosphonate when orally administered alone. The ratio of bisphosphonate to modified amino acid carrier according to the present invention may vary within limits. The ratio of bisphosphonate to modified amino acid carrier may be adjusted to the individual requirements in each particular case including the particular bisphosphonate being administered, the particular modified amino acid carrier being employed, the condition being treated, as well as the patient being treated. The ratio of bisphosphonate to modified amino acid carrier is preferably such that absorption of the orally administered bisphosphonate in the gastrointestinal tract is at least 2 times, preferably 3 times, more preferably 4 times, and most preferably 5 times greater than that of the bisphosphonate when orally administered alone. In general, in the case of oral administration to adult humans weighing approximately 70 Kg, the ratio of bisphosphonate to modified amino acid carrier, as measured by weight of each compound as the free acid in the pharmaceutical composition, is from about 1:30 to about 1:1, preferably about 1:20, more preferably about 1:10, and most preferably about 1:5, respectively.

The therapeutically effective amount or dosage of bisphosphonate according to this invention can vary within wide limits. Such dosage will be adjusted to the individual requirements in each particular case including the condition being treated, the patient being treated, as well as the specific bisphosphonate being administered.

For example, the recommended oral dose of ibandronate for the treatment of osteoporosis, when administered alone, to adult humans weighing approximately 70 Kg is 2.5 mg once daily, or 150 mg once monthly. In the present invention, the daily dose of ibandronate for the treatment of osteoporosis, when administered with a modified amino acid carrier, is lowered to from about 1.25 mg to about 0.25 mg, preferably from about 1 mg to about 0.4 mg, more preferably from about 0.65 mg to about 0.5 mg, and most preferably about 0.5 mg. The monthly dose of ibandronate for the treatment of osteoporosis, when administered with a modified amino acid carrier, is lowered to from about 75 mg to about 15 mg, preferably from about 60 mg to about 25 mg, more preferably from about 40 mg to about 30 mg, and most preferably about 30 mg.

The recommended oral dose of ibandronate for the treatment of hypercalcemia of cancer or the treatment of metastatic bone pain, when administered alone, to adult humans weighing approximately 70 Kg is 50 mg once daily. In the present invention, the daily dose of ibandronate for the treatment of hypercalcemia of cancer or the treatment of metastatic bone pain, when administered with a modified amino acid carrier, is lowered to from about 25 mg to about 5 mg, preferably from about 20 mg to about 8 mg, more preferably from about 13 mg to about 10 mg, and most preferably about 10 mg.

The anticipated oral dose of ibandronate for the treatment of hypercalcemia of cancer or the treatment of metastatic bone pain, when administered alone, to adult humans weighing approximately 70 Kg is 350 mg weekly. In the present invention, the anticipated weekly dose of ibandronate for the treatment of hypercalcemia of cancer or the treatment of metastatic bone pain, when administered with a modified amino acid carrier, is expected to be lowered to from about 175 mg to about 35 mg, preferably from about 140 mg to about 56 mg, more preferably from about 90 mg to about 70 mg, and most preferably about 70 mg.

The pharmaceutical dosage forms of the present invention may be prepared by simply admixing the bisphosphonate with the modified amino acid carrier prior to administration. The dosage forms may also be prepared by admixing an aqueous solution of the bisphosphonate with the modified amino acid carrier, just prior to administration. The solutions may optionally contain additives such as lactose monohydrate, croscarmellose sodium, povidone, water, sodium stearyl fumarate, and the like. Preferably, the solid pharmaceutical dosage form is prepared by intimately contacting the bisphosphonate with the modified amino acid carrier.

The dosage forms are preferably in tablet or capsule form. In one embodiment, the dosage form is a tablet and includes povidone. In another embodiment, the dosage form is a capsule and includes povidone. Povidone is preferably present in the dosage form in an amount from about 2% to about 30%, preferably from about 10% to about 20%, most preferably from about 12% to about 15%, by weight of the total composition.

The modified amino acid carriers may also be used to form microspheres containing the bisphosphonate. Microspheres are particularly useful for the oral administration of active agents, which do not pass, or only fractionally pass, through the gastrointestinal tract or are susceptible to chemical or enzymatic cleavage in the gastrointestinal tract. Methods for preparing microspheres are known and are disclosed, for example, in U.S. Pat. No. 5,650,386, which disclosure is incorporated herein by reference.

In another embodiment, the present invention provides a method for treating osteoporosis comprising orally administering to a subject, in need thereof, the novel solid pharmaceutical dosage form of the present invention. In yet another embodiment, the present invention provides a method for treating hypercalcemia of cancer comprising orally administering to a subject, in need thereof, the novel solid pharmaceutical dosage form of the present invention. In still yet another embodiment, the present invention provides a method for treating metastatic bone pain comprising orally administering to a subject, in need thereof, the novel solid pharmaceutical dosage form of the present invention.

In still yet another embodiment, the present invention provides a method for preparing a solid pharmaceutical dosage form for oral administration comprising admixing:

(a) a bisphosphonate, or a pharmaceutically acceptable salt thereof, which bisphosphonate is present in an amount not therapeutically effective when the bisphosphonate is orally administered alone; and (b) a modified amino acid carrier, or a pharmaceutically acceptable salt thereof, which modified amino acid carrier is present in an amount effective to facilitate absorption of the bisphosphonate in the gastrointestinal tract such that the bisphosphonate is therapeutically effective;

wherein the ratio of bisphosphonate to modified amino acid carrier is from about 1:30 to about 1:1, respectively.

In a preferred embodiment, the present invention provides an improved method for preparing the solid pharmaceutical dosage forms of the present invention. The method comprises providing the solid pharmaceutical dosage form wherein the bisphosphonate is in intimate contact with the modified amino acid carrier. Intimate contact is a close physical association between the bisphosphonate with the modified amino acid carrier and may be achieved by preparing the dosage form by granulation, spray drying, fluid bed coating, fluid bed layering, and the like.

The pharmaceutical dosage forms of the present invention can be prepared according to the examples set out below. The examples are presented for purposes of demonstrating, but not limiting, the preparation of the compounds and compositions of this invention.

EXAMPLES

In accordance with the present invention, the following examples are provided to illustrate solid pharmaceutical dosage forms, which utilize different ratios of bisphosphonate to modified amino acid carrier.

Example 1

In this example, 30 mg film coated ibandronic acid tablets were prepared wherein the ratio of ibandronic acid to sodium N-[8-(2-hydroxybenzoyl)amino]caprylate (SNAC) was 1:5.

Formulation Composition

| Item # | Ingredient | mg per Tablet |
|---|---|---|
| | Kernel Composition | |
| 1. | Ibandronate Monosodium Salt Monohydrate | 33.75[1] |
| 2. | Sodium N-[8-(2-hydroxybenzoyl)amino]caprylate | 161.81[2] |
| 3. | Lactose Monohydrate (Pharmatose ® 350) | 17.50 |
| 4. | Croscarmellose Sodium (Ac-Di-Sol ®) | 13.44 |
| 5. | Polyvinylpyrrolidone (Povidone; PVP K30) | 30.50 |
| 6. | Purified Water[3] | q.s. |
| 7. | Croscarmellose Sodium (Ac-Di-Sol ®) (External) | 9.25 |
| 8. | Sodium Stearyl Fumarate (External) | 3.75 |
| | Total Weight of Kernel | 270.00 |

-continued

| Item # | Ingredient | mg per Tablet |
|---|---|---|
| | Coating Composition | |
| 9. | Opadry White YS-1-7002 | 05.50 |
| 10. | Purified Water[3] | q.s. |
| | Total Weight of Film Coated Tablet | 275.50 |

[1]Equivalent to 30 mg of anhydrous ibandronic acid. The quantity of ibandronic acid is to be adjusted if the assay is less than 100%. If the assay adjustment is required, the quantity of Pharmatose ® 350 is reduced to compensate for the increase in ibandronic acid.
[2]Equivalent to 150 mg SNAC (anhydrous free acid).
[3]Removed during processing.

Method

Kernel Preparation Procedure

About 50% of sodium N-[8-(2-hydroxybenzoyl)amino]caprylate (SNAC) was placed in a PK blender or equivalent (Bin or Bohle mixer). Ibandronate monosodium salt monohydrate was then added to the mixture followed by the remainder of the SNAC. Pharmatose® 350, Ac-Di-Sol®, and PVP K30 were then added and the mixture was mixed for 15 minutes. The MFB-mini-fluid bed processor was set at the top spray set-up mode. The powder mix was then transferred into a MFB-mini-fluid bed processor. Fluidization was begun and the processor was pre-heated to 55° C. and the atomization pressure was set to less than 1 bar. The granulation process was started with the peristaltic pump using purified water as the granulating liquid. An initial amount equivalent to 20% w/w of the powder load was used and added over a period of 50±10 minutes. The inlet temperature was set to 55° C. with a range of 50° C.-60° C. Additional water may be added if necessary to achieve a consistent granulation. The peristaltic pump was then turned off to stop the granulation process. The granulation was then dried setting the inlet temperature at 60° C. with a range of 55° C.-65° C. Drying was continued until the moisture content was less than 1.5%. The dried granulation was milled using a FitzMill with screen #2, knives forward at medium speed. Sodium stearyl fumarate was pre-screened through a #30 mesh and the weight of the milled granulation was recorded and the weights of the external ingredients were adjusted: croscarmellose sodium (Ac-Di-Sol®) and the prescreened sodium stearyl fumarate. The milled granulation was transferred into a PK blender or equivalent and the adjusted amount of croscarmellose sodium (Ac-Di-Sol®) was added and the mixture was mixed for 20 minutes. About 50% of the mixed granulation was removed. The prescreened sodium stearyl fumarate was added to the remaining mixed granulation in the PK blender. The remainder of the mixed granulation was added and the mixture was mixed for 5 minutes. The final blend was compressed into kernels at a 270 mg weight (range of 260-280 mg). The kernels were stored in a tightly closed double polyethylene-lined container with 2 silica gel packets between the polyethylene bags.

Physical Product Specifications of the Kernel

| Tablet Tooling: | plain oval size 0.4865" × 0.257" |
|---|---|
| Tablet Weight (Target) | 270 mg |
| Tablet Weight (Range) | 260-280 mg |
| Tablet Thickness (Target) | 4.5 mm |

-continued

| | |
|---|---|
| Tablet Thickness (Range) | 4.0-5.0 mm |
| Tablet Hardness (Target) | 10 scu |
| Tablet Hardness (Range) | 8-15 scu |
| Disintegration Time (0.01 N HCl) | <20 minutes |
| Friability | <1.0% |

Film Coating Procedure

A film coating suspension was prepared having the following composition:

Film Coating Suspension

| Ingredient | % w/w |
|---|---|
| Opadry White YS-1-7002 | 8.00 |
| Purified Water q.s. | 100.00 |

In a stainless steel container, opadry white in purified water was dispersed by mixing gently (to avoid air entrapment) for 45 minutes with a Lightnin Mixer (300 rpm), until completely dispersed. The kernels were placed into a perforated coating pan and heated with warm inlet air of 45° C.±5° C. with intermittent jogging until the exhaust air temperature reached 40° C.±5° C. The inlet temperature was increased to 60° C.±5° C. and the kernels were coated with the coating suspension, stirred continuously, using an air spray system and maintaining the exhaust air temperature at 40° C.±5° C. A quantity of 5.5 mg of the film coat was applied on a dry basis, per tablet. The coated tablets were dried, with an inlet air temperature of 40° C.±5° C., by jogging until the moisture content of the tablets, determined by a Moisture Analyzer at 90° C., was less than 3%. The heat was then turned off and the tablets were cooled to room temperature by occasional jogging. The tablets were stored in a tightly closed double polyethylene-lined container with 2 silica gel packets between the polyethylene bags.

Example 2

In this example, 30 mg film coated ibandronic acid tablets were prepared wherein the ratio of ibandronic acid to sodium N-[8-(2-hydroxybenzoyl)amino]caprylate (SNAC) was 1:10.

Formulation Composition

| Item # | Ingredient | mg per Tablet |
|---|---|---|
| | Kernel Composition | |
| 1. | Ibandronate Monosodium Salt Monohydrate | 33.75[1] |
| 2. | Sodium N-[8-(2-hydroxybenzoyl)amino]caprylate | 323.63[2] |
| 3. | Lactose Monohydrate (Pharmatose ® 350) | 35.00 |
| 4. | Croscarmellose Sodium (Ac-Di-Sol ®) | 25.62 |
| 5. | Polyvinylpyrrolidone (Povidone; PVP K30) | 61.00 |
| 6. | Purified Water[3] | q.s. |
| 7. | Croscarmellose Sodium (Ac-Di-Sol ®) (External) | 18.50 |
| 8. | Sodium Stearyl Fumarate (External) | 7.50 |
| | Total Weight of Kernel | 505.00 |

| Item # | Ingredient | mg per Tablet |
|---|---|---|
| | Coating Composition | |
| 9. | Opadry White YS-1-7002 | 10.50 |
| 10. | Purified Water[3] | q.s. |
| | Total Weight of Film Coated Tablet | 515.50 |

[1]Equivalent to 30 mg of anhydrous ibandronic acid. The quantity of ibandronic acid is to be adjusted if the assay is less than 100%. If the assay adjustment is required, the quantity of Pharmatose ® 350 is reduced to compensate for the increase in ibandronic acid.
[2]Equivalent to 300 mg SNAC (anhydrous free acid).
[3]Removed during processing.

The method for preparing the kernel is similar to that set out in Example 1.

Physical Product Specifications of the Kernel

| | |
|---|---|
| Tablet Tooling: | plain oval size 0.2945" × 0.558" |
| Tablet Weight (Target): | 505 mg |
| Tablet Weight (Range): | 490-520 mg |
| Tablet Thickness (Target): | 6.00 mm |
| Tablet Thickness (Range): | 5.5-6.5 mm |
| Tablet Hardness (Target): | 15 scu |
| Tablet Hardness (Range): | 10-20 scu |
| Disintegration Time (0.01 N HCl): | <20 minutes |
| Friability: | <1.0% |

Film Coating Procedure

A film coating suspension was prepared having the following composition:

Film Coating Suspension

| Ingredient | % w/w |
|---|---|
| Opadry White YS-1-7002 | 8.00 |
| Purified Water q.s. | 100.00 |

The film coating suspension was prepared in a manner similar to that set out in Example 1.

Example 3

In this example, 30 mg film coated ibandronic acid tablets were prepared wherein the ratio of ibandronic acid to sodium N-[8-(2-hydroxybenzoyl)amino]caprylate (SNAC) was 1:20.

Formulation Composition

| Item # | Ingredient | mg per Tablet |
|---|---|---|
| | Kernel Composition | |
| 1. | Ibandronate Monosodium Salt Monohydrate | 33.75[1] |
| 2. | Sodium N-[8-(2-hydroxybenzoyl)amino]caprylate | 647.25[2] |
| 3. | Lactose Monohydrate (Pharmatose ® 350) | 70.00 |
| 4. | Croscarmellose Sodium (Ac-Di-Sol ®) | 50.00 |
| 5. | Polyvinylpyrrolidone (Povidone; PVP K30) | 122.00 |

-continued

| Item # | Ingredient | mg per Tablet |
|---|---|---|
| 6. | Purified Water[3] | q.s. |
| 7. | Croscarmellose Sodium (Ac-Di-Sol ®) (External) | 37.00 |
| 8. | Sodium Stearyl Fumarate (External) | 15.00 |
| | Total Weight of Kernel Coating Composition | 975.00 |
| 9. | Opadry White YS-1-7002 | 20.00 |
| 10. | Purified Water[3] | q.s. |
| | Total Weight of Film Coated Tablet | 995.00 |

[1]Equivalent to 30 mg of anhydrous ibandronic acid. The quantity of ibandronic acid is to be adjusted if the assay is less than 100%. If the assay adjustment is required, the quantity of Pharmatose ® 350 is reduced to compensate for the increase in ibandronic acid.
[2]Equivalent to 600 mg SNAC (anhydrous free acid).
[3]Removed during processing.

The method for preparing the kernel is similar to that set out in Example 1.

Physical Product Specifications of the Kernel

| | |
|---|---|
| Tablet Tooling: | plain oval size 0.827" × 0.317" |
| Tablet Weight (Target): | 975 mg |
| Tablet Weight (Range): | 945-1005 mg |
| Tablet Thickness (Target): | 7.00 mm |
| Tablet Thickness (Range): | 6.5-7.5 mm |
| Tablet Hardness (Target): | 20 scu |
| Tablet Hardness (Range): | 15-25 scu |
| Disintegration Time (0.01 N HCl): | <20 minutes |
| Friability: | <1.0% |

Film Coating Procedure

A film coating suspension was prepared having the following composition:

Film Coating Suspension

| Ingredient | % w/w |
|---|---|
| Opadry White YS-1-7002 | 8.00 |
| Purified Water q.s. | 100.000 |

The film coating suspension was prepared in a manner similar to that set out in Example 1.

Example 4

In this example, 30 mg film coated ibandronic acid tablets were prepared wherein the ratio of ibandronic acid to sodium N-[8-(2-hydroxybenzoyl)amino]caprylate (SNAC) was 1:5.

Formulation Composition

| Item # | Ingredient | mg per Tablet |
|---|---|---|
| | Kernel Composition | |
| 1. | Ibandronate Monosodium Salt Monohydrate | 33.75[1] |
| 2. | Sodium N-[8-(2-hydroxybenzoyl)amino]caprylate | 161.81[2] |
| 3. | Lactose Monohydrate (Pharmatose ® 350) | 17.50 |

-continued

| Item # | Ingredient | mg per Tablet |
|---|---|---|
| 4. | Croscarmellose Sodium (Ac-Di-Sol ®) | 13.44 |
| 5. | Polyvinylpyrrolidone (Povidone; PVP K30) | 30.50 |
| 6. | Purified Water[3] | q.s. |
| 7. | Croscarmellose Sodium (Ac-Di-Sol ®) (External) | 9.25 |
| 8. | Sodium Stearyl Fumarate (External) | 3.75 |
| | Total Weight of Kernel Coating Composition | 270.00 |
| 9. | Opadry White YS-1-7002 | 5.50 |
| 10. | Purified Water[3] | q.s. |
| | Total Weight of Film Coated Tablet | 275.50 |

[1]Equivalent to 30 mg of anhydrous ibandronic acid. The quantity of ibandronic acid is to be adjusted if the assay is less than 100%. If the assay adjustment is required, the quantity of Pharmatose ® 350 is reduced to compensate for the increase in ibandronic acid.
[2]Equivalent to 150 mg SNAC (anhydrous free acid).
[3]Removed during processing.

Using a propeller mixer or a homogenizer-mixer set at slow speed, ibandronate monosodium salt monohydrate was dissolved in purified water to form a 33% w/w solution (warm at 45° C. ranges 40 to 50° C., if necessary to help dissolving the drug). The drug was added in small portions while maintaining a slow speed during mixing to avoid foam formation. Sodium N-[8-(2-hydroxybenzoyl)amino]caprylate (SNAC) was placed in a PK blender or equivalent (Bin or Bohle mixer). Pharmatose® 350, Ac-Di-Sol®, and PVP $K_{30}$ were then added and mixed for 20 minutes. The MFB-mini-fluid bed processor was set at the Top Spray set-up mode. The powder mix was transferred into the MFB-mini-fluid bed processor. The process of fluidization was started and the processor pre-heated at a temperature of 50° C. The atomization pressure was set to less than 1 bar. With the peristaltic pump set at a slow speed, the granulation process was started using the solution of the drug in purified water as the granulating liquid. The solution was added over a period of 45 minutes (range 30-60 minutes). The inlet temperature was targeted to 50° C., with a range of 45 to 55° C. Additional water was added if necessary to achieve a consistent granulation. The granulation process was stopped by turning off the peristaltic pump. The granulation was started setting the inlet temperature range at 55-60° C. Drying was continued until the moisture content (loss on drying), as measured by moisture analyzer set at 90° C., was less than 1.5%. The dried granulation was milled using a FitzMill with screen #2, knives forward at medium speed. Sodium stearyl fumarate was prescreened through #30 mesh. The weight of the milled granulation was recorded and the weight of the external ingredients was adjusted: Croscarmellose Sodium Ac-Di-Sol® and the prescreened Sodium stearyl fumarate. The milled granulation was transferred into a PK blender or equivalent. The adjusted amount of Croscarmellose Sodium (Ac-Di-Sol®) was added and mixed for 20 minutes. About 50% of the mixed granulation was removed. The prescreened Sodium Stearyl Fumarate was added to the remaining mixed granulation in the PK blender. The remaining portion of the mixed granulation removed was added and mixed for 5 minutes. The final blend was compressed into kernels at 270 mg weight (range of 260-280 mg). The kernels were stored in a tightly closed polyethylene-lined container with 2 silica gel packets between the polyethylene bags.

Physical Product Specifications of the Kernel

| Tablet Tooling: | plain oval size 0.4865" × 0.257" |
|---|---|
| Tablet Weight (Target) | 270 mg |
| Tablet Weight (Range) | 260-280 mg |
| Tablet Thickness (Target) | 4.5 mm |
| Tablet Thickness (Range) | 4.0-5.0 mm |
| Tablet Hardness (Target) | 10 scu |
| Tablet Hardness (Range) | 8-15 scu |
| Disintegration Time (0.01 N HCl) | <20 minutes |
| Friability | <1.0% |

Film Coating Procedure

A film coating suspension was prepared having the following composition:

Film Coating Suspension

| Ingredient | % w/w |
|---|---|
| Opadry White YS-1-7002 | 8.00 |
| Purified Water q.s. | 100.00 |

In a stainless steel container, opadry white in purified water was dispersed by mixing (gently to avoid air entrapment) for 45 minutes with a Lightnin Mixer (300 rpm), until completely dispersed. The kernels were placed into a perforated coating pan and heated with warm inlet air of 45° C.±5° C. with intermittent jogging until the exhaust air temperature reached 40° C.±5° C. The inlet temperature was increased to 60° C.±5° C. and the kernels were coated with the coating suspension, stirred continuously, using an air spray system and maintaining the exhaust air temperature at 40° C.±5° C. A quantity of 5.5 mg of the film coat was applied on a dry basis, per tablet. The coated tablets were dried, with an inlet air temperature of 40° C.±5° C., by jogging until the moisture content of the tablets, determined by a Moisture Analyzer at 90° C., was less than 3%. The heat was then turned off and the tablets were cooled to room temperature by occasional jogging. The tablets were stored in a tightly closed double polyethylene-lined container with 2 silica gel packets between the polyethylene bags.

Example 5

In this example, 30 mg film coated ibandronic acid tablets were prepared wherein the ratio of ibandronic acid to sodium N-[8-(2-hydroxybenzoyl)amino]caprylate (SNAC) was 1:10.

Formulation Composition

| Item # | Ingredient | mg per Tablet |
|---|---|---|
| | Kernel Composition | |
| 1. | Ibandronate Monosodium Salt Monohydrate | 33.75[1] |
| 2. | Sodium N-[8-(2-hydroxybenzoyl)amino]caprylate | 323.63[2] |
| 3. | Lactose Monohydrate (Pharmatose ® 350) | 35.00 |
| 4. | Croscarmellose Sodium (Ac-Di-Sol ®) | 25.62 |
| 5. | Polyvinylpyrrolidone (Povidone; PVP K30) | 61.00 |
| 6. | Purified Water[3] | q.s. |
| 7. | Croscarmellose Sodium (Ac-Di-Sol ®) (External) | 18.50 |
| 8. | Sodium Stearyl Fumarate (External) | 7.50 |
| | Total Weight of Kernel | 505.00 |
| | Coating Composition | |
| 9. | Opadry White YS-1-7002 | 10.50 |
| 10. | Purified Water[3] | q.s. |
| | Total Weight of Film Coated Tablet | 515.50 |

[1]Equivalent to 30 mg of anhydrous ibandronic acid. The quantity of ibandronic acid is to be adjusted if the assay is less than 100%. If the assay adjustment is required, the quantity of Pharmatose ® 350 is reduced to compensate for the increase in ibandronic acid.
[2]Equivalent to 300 mg SNAC (anhydrous free acid).
[3]Removed during processing.

The method for preparing the kernel is similar to that set out in Example 4.

Physical Product Specifications of the Kernel

| Tablet Tooling: | plain oblong size 0.33" × 0.625" |
|---|---|
| Tablet Weight (Target): | 505 mg |
| Tablet Weight (Range): | 490-520 mg |
| Tablet Thickness (Target): | 6.00 mm |
| Tablet Thickness (Range): | 5.5-6.5 mm |
| Tablet Hardness (Target): | 12 scu |
| Tablet Hardness (Range): | 10-15 scu |
| Disintegration Time (0.01 N HCl): | <20 minutes |
| Friability: | <1.0% |

Film Coating Procedure

A film coating suspension was prepared having the following composition:

Film Coating Suspension

| Ingredient | % w/w |
|---|---|
| Opadry White YS-1-7002 | 8.00 |
| Purified Water q.s. | 100.00 |

The film coating suspension was prepared in a manner similar to that set out in Example 4.

Example 6

In this example, 30 mg film coated ibandronic acid tablets were prepared wherein the ratio of ibandronic acid to sodium N-[8-(2-hydroxybenzoyl)amino]caprylate (SNAC) was 1:20.

Formulation Composition

| Item # | Ingredient | mg per Tablet |
|---|---|---|
| | Kernel Composition | |
| 1. | Ibandronate Monosodium Salt Monohydrate | 33.75[1] |
| 2. | Sodium N-[8-(2-hydroxybenzoyl)amino]caprylate | 647.25[2] |
| 3. | Lactose Monohydrate (Pharmatose ® 350) | 70.00 |

-continued

| Item # | Ingredient | mg per Tablet |
|---|---|---|
| 4. | Croscarmellose Sodium (Ac-Di-Sol ®) | 50.00 |
| 5. | Polyvinylpyrrolidone (Povidone; PVP K30) | 122.00 |
| 6. | Purified Water[3] | q.s. |
| 7. | Croscarmellose Sodium (Ac-Di-Sol ®) (External) | 37.00 |
| 8. | Sodium Stearyl Fumarate (External) | 15.00 |
| | Total Weight of Kernel | 975.00 |
| | Coating Composition | |
| 9. | Opadry White YS-1-7002 | 20.00 |
| 10. | Purified Water[3] | q.s. |
| | Total Weight of Film Coated Tablet | 995.00 |

[1]Equivalent to 30 mg of anhydrous ibandronic acid. The quantity of ibandronic acid is to be adjusted if the assay is less than 100%. If the assay adjustment is required, the quantity of Pharmatose ® 350 is reduced to compensate for the increase in ibandronic acid.
[2]Equivalent to 600 mg SNAC (anhydrous free acid).
[3]Removed during processing.

The method for preparing the kernel is similar to that set out in Example 4.

Physical Product Specifications of the Kernel

| | |
|---|---|
| Tablet Tooling: | plain oval size 0.827" × 0.317" |
| Tablet Weight (Target): | 975 mg |
| Tablet Weight (Range): | 945-1005 mg |
| Tablet Thickness (Target): | 7.00 mm |
| Tablet Thickness (Range): | 6.5-7.5 mm |
| Tablet Hardness (Target): | 16 scu |
| Tablet Hardness (Range): | 13-25 scu |
| Disintegration Time (0.01 N HCl): | <30 minutes |
| Friability: | <1.0% |

Film Coating Procedure

A film coating suspension was prepared having the following composition:

Film Coating Suspension

| Ingredient | % w/w |
|---|---|
| Opadry White YS-1-7022 | 8.00 |
| Purified Water q.s. | 100.000 |

The film coating suspension was prepared in a manner similar to that set out in Example 4.

Example 7

In this example, 30 mg ibandronic acid capsules were prepared wherein the ratio of ibandronic acid to sodium N-[8-(2-hydroxybenzoyl)amino]caprylate (SNAC) was 1:5.

Formulation Composition

| Item # | Ingredient | mg per Capsule |
|---|---|---|
| | Drug Layering | |
| 1. | Ibandronate Monosodium Salt Monohydrate[1] | 33.750[2] |
| 2. | Sodium N-[8-(2-hydroxybenzoyl)amino]caprylate | 161.810[3] |
| 3. | Kollidon ® 12PF (povidone) | 9.780 |
| 4. | Altalc 500 | 9.780 |
| 5. | Cellets 200 (microcrystalline cellulose) | 53.780 |
| 6. | Purified Water | (501.950)[4] |
| | Seal Coat | |
| 7. | Kollidon ® 12PF (povidone) | 0.135 |
| 8 | Zeopharm 600 | 2.565 |
| 9. | Purified Water | (51.300)[4] |
| | Capsule Fill Weight | 271.600 |
| | Encapsulation | |
| 10. | White Opaque Hard Gelatin Capsule #2 | 61.00[5] |
| | Total Weight of Capsule | 332.600 |

[1]Fine Powder.
[2]Equivalent to 30 mg of anhydrous ibandronic acid. The quantity of ibandronic acid is to be adjusted if the assay is less than 100%. If the assay adjustment is required, the quantity of Cellets 200 is reduced to compensate for the increase in ibandronic acid.
[3]Equivalent to 150 mg SNAC (anhydrous free acid).
[4]Removed during processing.
[5]Target capsule weight.

Method

Drug Layering Procedure
Preparation of the Drug Layering Suspension

In a stainless steel container, Kollidon 12 PF was added to purified water while mixing using a propeller mixer at medium speed. Mixing was continued until the Kollidon 12 PF was completely dissolved. Ibandronate Monosodium Salt Monohydrate was added to the solution while mixing at medium speed. Mixing was continued until the drug was completely dissolved. SNAC was added to the solution while mixing at medium speed. Mixing was continued for at least 1 hour or until a uniform dispersion was obtained. The suspension was then transported in tightly closed containers to Glatt Air Techniques. Altalc 500 was added to the suspension while mixing using a propeller mixer at medium speed. Mixing was continued for at least 1 hour or until a uniform dispersion was obtained. A portion (approximately 2-liters) of the coating suspension was warmed in a jacketed vessel equilibrated at 50°±5° C., while mixing using a propeller mixer at medium speed. The remainder of the suspension was mixed using a propeller mixer at medium speed.

Application of the Drug Layering Suspension

The quantity of Cellets 200 was placed into a fluid bed coater with a Wurster HS insert. The Cellets 200 was warmed for at least 2 minutes with inlet air temperature of 70±10° C., providing sufficient air volume to fluidize the Cellets 200. The warm drug layering suspension was sprayed, with continuous mixing using a propeller mixer at medium speed, to the Cellets 200 using the following processing conditions:

| | |
|---|---|
| Inlet temperature | 70° ± 10° C. |
| Target product temperature | 50° C. (Range: 35°-55° C.) |
| Nozzle orifice | 1.2 mm |
| Atomization air pressure | 3.0 ± 1.0 Bar |
| Partition Height: | 20 mm |

The air volume used to fluidize the Cellets 200 was recorded.

The drug layering suspension was re-supplied to maintain its volume (approximately 2-liters) throughout the coating process by pumping the coating suspension at the rate comparable to the coating spray rate. A quantity of 215.120 mg per capsule (on a dry basis) of the drug layering suspension was applied per 53.780 mg per capsule of the Cellets 200.

Seal Coating Procedure

Preparation of the Seal Coating Suspension

In a stainless steel container, Kollidon 12 PF was added to purified water while mixing using a propeller mixer at medium speed. Mixing was continued until the Kollidon 12 PF was completely dissolved. The solution was transported in a tightly closed container to Glatt Air Techniques. Zeopharm 600 was added to the solution while mixing using a propeller mixer at medium speed for at least 30 minutes or until a uniform dispersion was obtained.

Application of the Seal Coating Suspension

The seal coating suspension was sprayed, with continuous mixing using a propeller mixer at medium speed, to the drug layered beadlets using the following processing conditions:

| Inlet temperature | 60° ± 10° C. |
|---|---|
| Target product temperature | 40° C. (Range: 30°-50° C.) |
| Nozzle orifice | 1.2 mm |
| Atomization air pressure | 3.0 ± 1.0 Bar |
| Partition Height: | 20 mm |

The air volume used to fluidize the beadlets was recorded.

A quantity of 2.7 mg per capsule (on a dry basis) of the seal coat was applied per 268.9 mg per capsule of the drug layered beadlets.

The seal coated beadlets were dried using an inlet air temperature of 600±10° C. until the moisture content of the beadlets, determined by the Karl Fisher Method, was less than 2% w/w. The beadlets were cooled to obtain a product temperature of 40°±5° C. by turning off process air heat. The beadlets were discharged into a double polyethylene lined fiber drum. The finished beadlets were shipped in double polyethylene bags in a closed fiber drum with two silica gel bags between the polyethylene bags at 25° C. (77° F.) for encapsulation.

Encapsulation

Using a capsule filling machine, the beadlets were filled into white opaque hard gelatin capsules, size #2, at a target weight of 271.6 mg/capsule (Range: 258.0-285.2 mg/capsule). The finished capsules were stored in double polyethylene bags in a closed fiber drum with two silica gel bags between the polyethylene bags at 25° C. (range permitted to 15°-30° C.).

Example 8

In this example, 30 mg ibandronic acid capsules were prepared wherein the ratio of ibandronic acid to sodium N-[8-(2-hydroxybenzoyl)amino]caprylate (SNAC) was 1:10.

Formulation Composition

| Item # | Ingredient | mg per Capsule |
|---|---|---|
| | Drug Layering | |
| 1. | Ibandronate Monosodium Salt Monohydrate[1] | 33.750[2] |
| 2. | Sodium N-[8-(2-hydroxybenzoyl)amino]caprylate | 323.630[3] |
| 3. | Kollidon ® 12PF (povidone) | 17.870 |
| 4. | Altalc 500 | 17.870 |
| 5. | Cellets 200 (microcrystalline cellulose) | 98.280 |
| 6. | Purified Water | (917.260)[4] |
| | Seal Coat | |
| 7. | Kollidon ® 12PF (povidone) | 0.250 |
| 8 | Zeopharm 600 | 4.650 |
| 9. | Purified Water | (93.480)[4] |
| | Capsule Fill Weight | 496.300 |
| | Encapsulation | |
| 10. | White Opaque Hard Gelatin Capsule #0 | 96.00[5] |
| | Total Weight of Capsule | 592.300 |

[1]Fine Powder.

[2]Equivalent to 30 mg of anhydrous ibandronic acid. The quantity of ibandronic acid is to be adjusted if the assay is less than 100%. If the assay adjustment is required, the quantity of Cellets 200 is reduced to compensate for the increase in ibandronic acid.

[3]Equivalent to 300 mg SNAC (anhydrous free acid).

[4]Removed during processing.

[5]Target capsule weight.

The capsule forming procedure was prepared in a manner similar to that set out in Example 7.

Example 9

In this example, 15 mg ibandronic acid capsules were prepared wherein the ratio of ibandronic acid to sodium N-[8-(2-hydroxybenzoyl)amino]caprylate (SNAC) was 1:20.

Formulation Composition

| Item # | Ingredient | mg per Capsule |
|---|---|---|
| | Drug Layering | |
| 1. | Ibandronate Monosodium Salt Monohydrate[1] | 16.875[2] |
| 2. | Sodium N-[8-(2-hydroxybenzoyl)amino]caprylate | 323.630[3] |
| 3. | Kollidon ® 12PF (povidone) | 17.025 |
| 4. | Altalc 500 | 17.025 |
| 5. | Cellets 200 (microcrystalline cellulose) | 93.640 |
| 6. | Purified Water | (873.962)[4] |
| | Seal Coat | |
| 7. | Kollidon ® 12PF (povidone) | 0.234 |
| 8 | Zeopharm 600 | 4.446 |
| 9. | Purified Water | (88.920)[4] |
| | Capsule Fill Weight | 472.875 |
| | Encapsulation | |
| 10. | White Opaque Hard Gelatin Capsule #0 | 96.00[5] |
| | Total Weight of Capsule | 568.875 |

[1]Fine Powder.

[2]Equivalent to 15 mg of anhydrous ibandronic acid. The quantity of ibandronic acid is to be adjusted if the assay is less than 100%. If the assay adjustment is required, the quantity of Cellets 200 is reduced to compensate for the increase in ibandronic acid.

[3]Equivalent to 300 mg SNAC (anhydrous free acid).

[4]Removed during processing.

[5]Target capsule weight.

The capsule forming procedure was prepared in a manner similar to that set out in Example 7.

Example 10

In this example, 30 mg hard gelatin capsules are made using a powder mixture of SNAC and ibandronate.

Formulation Composition

| Item # | | mg per capsule |
|---|---|---|
| 1. | Ibandronate Monosodium Salt Monohydrate[1] | 33.75[2] |
| 2. | Sodium N-[8-(2-hydroxybenzoyl)amino]caprylate (SNAC) | 161.81[3] |
| 3. | Croscarmellose Sodium (Ac-Di-Sol) | 1.50 |
| 4. | Polyvinylpyrrolidone (Povidone; PVP K30) | 12.14 |
| 5. | Purified Water | Qs. ad.[4] |
| 6. | Calcium Silicate (Zeopharm 600) (External) | 2.00 |
| 7. | Croscarmellose Sodium (Ac-Di-Sol) (External) | 1.50 |
| 8. | Sodium Stearyl Fumarate | 4.30 |
| | Total Weight of Capsule Fill | 217.00 |
| 9. | White Opaque Hard Gelatin Capsule #1 | |

[1] Fine powder
[2] Equivalent to 30 mg anhydrous Ibandronic Acid. The quantity of ibandronate sodium is to be adjusted if the assay is less than 100%. If the assay adjustment is required, the quantity of PVP K30 is reduced to compensate for the increase in ibandronate sodium.
[3] Equivalent to 150 mg SNAC (anhydrous free acid)
[4] Removed during processing About 50% of the total quantity of Sodium N-[8-(2-hydroxybenzoyl)amino]caprylate (SNAC) (item 2) is placed in a mixer, such as a PK blender or the equivalent (Bin or Bohle mixer). Ibandronate sodium (item 1), the remainder of SNAC, Ac-Di-Sol (item 3), and PVP K30 (item 4) are added and the components are mixed for 15 minutes to yield a powder mix. A MP 2/3 fluid bed processor at the Top Spray mode is set up. The powder mix is transferred into the MP 2/3 fluid bed processor. The process of fluidization is started and the processor is pre-heated to a temperature of 55° C. The atomization pressure is set to less than 1 bar. Using a peristaltic pump, the granulation process is started using Purified Water as the granulating liquid, using an initial amount equivalent to 30% w/w of the powder load and added over a period of 45±15 minutes. An inlet temperature target of 60° C. with a range of 55° to 65° C. is set. Additional water is added as necessary to achieve a consistent granulation.

The granulation process is stopped by turning off the peristaltic pump. The granulation is dried by setting the inlet temperature at 65° C. with a range of 65° to 70° C., and is continued until the moisture content (loss on drying), as measured by a moisture analyzer set at 90° C., is less than 1.5%. The dried granulation is milled using a Comill with screen #055R, at a speed of 1500 rpm (range 1400 rpm to 1800 rpm), to yield a milled granulation. Zeopharm (item 6) and sodium stearyl fumarate (item 8) are separately screened through a #40 mesh screen. The weight of the milled granulation is recorded and the weights of the Zeopharm (item #6), Croscarmellose Sodium (Ac-Di-Sol) (item 7) and Sodium Stearyl Fumarate (item 8) are adjusted to their correct proportions. The milled granulation is transferred into a PK blender or equivalent. The adjusted amounts of prescreened Zeopharm and Croscarmellose Sodium (Ac-Di-Sol) are added and mixed for 20 minutes to yield a mixed granulation, and then about 50% of the mixed granulation is removed. The prescreened Sodium Stearyl Fumarate is added to the remaining 50% of the mixed granulation in the PK blender, followed by the addition of the portion of the mixed granulation previously removed, followed by mixing for 5 minutes to yield a final blend. This final blend is filled into #1 white opaque hard gelatin capsules (item 9) at a target weight of 217 mg (range 210 mg to 225 mg). Filled capsules are stored in polyethylene double bags in fiber drums with 2 silica gel packets between the bags.

Physical Product Specifications

| | |
|---|---|
| Capsule Fill Weight (Target): | 217 mg |
| Capsule Fill Weight (Range): | 210-225 mg |
| Disintegration Time (0.01 N HCl): | <10 minutes |

While a number of embodiments of this invention have been represented, it is apparent that the basic construction can be altered to provide other embodiments that utilize the invention without departing from the spirit and scope of the invention. All such modifications and variations are intended to be included within the scope of the invention as defined in the appended claims rather than the specific embodiments that have been presented by way of example.

We claim:

1. A method for treating hypercalcemia of cancer comprising orally administering to a subject in need thereof a solid pharmaceutical dosage form comprising about 33.8 mg alendronate sodium, about 161.8 mg sodium N-(8-(2-hydroxybenzoyl)amino)caprylate, about 17.5 mg lactose monohydrate, about 13.4 mg croscarmellose sodium, about 30.5 mg polyvinylpyrrolidone and about 3.8 mg sodium stearyl fumarate.

2. A method for treating hypercalcemia of cancer comprising orally administering to a subject in need thereof a solid pharmaceutical dosage form comprising about 33.8 mg alendronate sodium, about 161.8 mg sodium N-(8-(2-hydroxybenzoyl)amino)caprylate, about 9.8 mg povidone, about 9.8 mg talc and about 53.8 mg microcrystalline cellulose.

3. A method for treating hypercalcemia of cancer comprising orally administering to a subject in need thereof a solid pharmaceutical dosage form comprising about 33.8 mg alendronate sodium, about 161.8 mg sodium N-(8-(2-hydroxybenzoyl)amino)caprylate, about 1.5 mg croscarmellose sodium, about 12.1 mg polyvinylpyrrolidone, about 2.0 mg calcium silicate and about 4.3 mg sodium stearyl fumarate.

* * * * *